United States Patent [19]
Radford et al.

[11] Patent Number: 5,362,714
[45] Date of Patent: Nov. 8, 1994

[54] PROCESS FOR DEWAXING CITRUS OILS

[75] Inventors: Terence Radford, Dunwoody; Ad S. Olansky, Decatur, both of Ga.

[73] Assignee: The Coca-Cola Company, Atlanta, Ga.

[21] Appl. No.: 83,929

[22] Filed: Jun. 29, 1993

[51] Int. Cl.$^5$ ............................................. A61K 7/46
[52] U.S. Cl. ...................................... 512/5; 426/651; 424/195.1; 514/783
[58] Field of Search ............................ 512/5; 426/651; 424/95.1

[56] References Cited

U.S. PATENT DOCUMENTS

| | | | |
|---|---|---|---|
| 3,037,975 | 6/1962 | Cohn | 426/651 |
| 3,155,648 | 11/1964 | Swisher | 426/651 |
| 3,915,960 | 10/1975 | Jefferson et al. | 426/651 |
| 4,093,565 | 6/1978 | Steltenkamp | 512/5 |

FOREIGN PATENT DOCUMENTS

| | | | |
|---|---|---|---|
| 56-70096 | 6/1981 | Japan | 512/5 |
| 63-89594 | 4/1988 | Japan | 512/5 |

*Primary Examiner*—James H. Reamer
*Attorney, Agent, or Firm*—Kenyon & Kenyon

[57] ABSTRACT

A process for transforming and removing latent sediment-forming components from citrus oils to supplement a dewaxing process for the citrus oils. Psoralen epoxides in citrus oils are converted to diols in an accelerated and controlled manner. The epoxide-to-diol transformation is effected by mixing citrus oil with an aqueous acidic treatment solution under conditions (i.e., solution pH and volume) and for a sufficient period of time to convert substantially all of the psoralen epoxides. The diols formed thereby are precipitated and/or preferentially dissolved in the aqueous phase during mixing. Upon separation of the aqueous phase from the oil, the citrus oil is substantially free of psoralen epoxides. By this method, epoxides are inexpensively eliminated from the citrus oils, resulting in an improved product having, for example, reduced sedimentation potential and reduced phototoxicity.

36 Claims, No Drawings

PROCESS FOR DEWAXING CITRUS OILS

BACKGROUND OF THE INVENTION

1. Field of the Invention

The invention relates to a method for removing sediment-forming materials, such as nonvolatile components ("waxes"), from citrus oils. More particularly, the invention relates to a process for eliminating latent waxes by treating citrus oils with an aqueous acidic treatment solution.

2. Description of Related Art

A well-known problem with cold-pressed citrus oils is that they tend to develop sediments during storage. Formation of these sediments is primarily attributable to the presence of certain nonvolatile components in the oils, commonly and generically referred to as "waxes". The removal of sediments can be a tedious and expensive process. Therefore, the art has searched for ways to reduce the wax content of citrus oils, and thereby minimize sediment formation. Unfortunately, no method known to date has proven to be completely effective.

The most common commercial "dewaxing" procedure involves chilling freshly-produced citrus oil well below its normal storage temperature. By chilling the oil, the solubility of the waxes present in the oil is reduced and some of the waxes tend to precipitate out of solution. The precipitates are then removed by centrifuging the chilled oil. A soluble portion of the waxes, however, remains in the oil after this process.

If the soluble waxes remaining in the citrus oil were not susceptible to any subsequent chemical changes, this commercial dewaxing procedure would provide a shelf-stable citrus oil, because these waxes would remain soluble indefinitely at normal storage temperatures. However, a principal weakness of this procedure is that some of the waxes do undergo chemical changes during storage. For example, psoralen epoxides, which are relatively soluble in cold citrus oils and thus are not removed by chilling-dewaxing, gradually undergo hydrolysis in solution to yield the corresponding diols. These diols are much less soluble than their epoxide precursors in the citrus oil, and they precipitate. In a typical citrus oil kept under typical storage conditions, this transformation occurs slowly but continuously, resulting in increasing amounts of sediment deposition over a period of weeks to years.

Some of the psoralen epoxides not removed by chilling are also known to be phototoxic, making some commercially-available citrus oils unsuitable for use in fragrances and other products applied to the skin.

Attempts have been made to improve upon conventional chilling-dewaxing processes. U.S. Pat. No. 2,863,861 to Platt describes a process for treating citrus oils to remove "wax-crystallization-inhibiting" compounds ("inhibitors") prior to conventional dewaxing by chilling (i.e., chilling, brief cold storage and centrifugation). These unidentified compounds are said to inhibit the crystallization or separation out of waxes in citrus oils during chilling, thereby impairing the effectiveness of wax removal by chilling. In the described process, the citrus oil is washed with a buffered aqueous dispersion of an active esterase or pectase enzyme which is claimed to be capable of destroying the inhibitors, for a period of time deemed sufficient to allow the enzyme to act on and destroy the inhibitors. The enzyme dispersion is buffered to a pH ranging from 4.0 to 7.0 using sodium citrate and citric acid. The washed oil is then separated from the aqueous portion.

The method of U.S. Pat. No. 2,863,861 specifically addresses the problem of wax-crystallization-inhibiting compounds; however, it does not address nor even recognize the separate problem of the conversion of oil-soluble psoralen epoxides to insoluble diols during storage of the citrus oil. The method is not effective in preventing the development of sediments during subsequent storage of the treated citrus oils, because the method does not reduce nor eliminate the amount of psoralen epoxides in the citrus oil. The prior art's lack of effectiveness in this respect has been confirmed by high performance liquid chromatography (HPLC) analysis, which allows for measurement of the epoxide and diol concentrations in citrus oil before and after processing.

Japanese Patent Laid-Open No. 84457/1988 discloses a process for removing phototoxic furocoumarins (psoralens) from lemon oil. In this method, lemon oil is first distilled at reduced pressure to remove any furocoumarins from the distillate. The residue is then dissolved in a solvent and reduced with LiAlH$_4$. Water is then added to decompose the LiAlH$_4$, followed by solvent extraction and subsequent distillation to remove the extraction solvent. The residue of the second distillation is then combined with the distillate from the first distillation to yield the final product.

This complex technique is expensive due to the need for costly reagents and energy-intensive separation techniques. In addition, the method can cause undesirable changes in the volatiles content and hence the flavor of the oil due to the distillation process.

SUMMARY OF THE INVENTION

Accordingly, it is an object of the invention to provide an effective and inexpensive process for removing potential sediment-forming components, such as psoralen epoxides, from citrus oils.

It is a further object of the invention to provide such a process which does not require treating the citrus oil with esterase or pectase enzymes.

It is another object of the invention to supplement and improve conventional chilling-dewaxing processes for citrus oils by eliminating latent sediment-forming components, such as psoralen epoxides, from the citrus oils.

It is yet another object of the invention to provide a dewaxing process for citrus oils which yields sediment-free oil which will remain sediment-free indefinitely during storage.

These and other objects are achieved by the invention which, in one embodiment, is a process for dewaxing citrus oils which comprises the step of vigorously mixing a citrus oil with an acidic aqueous treatment solution under conditions and for a period of time which is sufficient to convert substantially all psoralen epoxides in the citrus oil to the corresponding diols, thereby precipitating (or extracting) the diols from the oil. After mixing, the acidic aqueous treatment solution (i.e., aqueous phase) will contain solubilized psoralen diols, and the citrus oil, now substantially free of psoralen epoxides, is separated from the aqueous phase and isolated.

The acidic aqueous treatment solution preferably comprises water and an amount of citric acid effective to produce a pH of less than 3, preferably less than 1. The acidic aqueous treatment solution may be added to the citrus oil prior to mixing (as in the case of a finished oil) or formed in situ by adding solid citric acid to an emulsion of citrus oil and water (as in the case of an incompletely processed oil). The acidic aqueous treatment solution most preferably consists of about 50 weight % citric acid and 50 weight % water which results in a solution having a pH of about 0.5.

The invention is designed to supplement conventional chilling-dewaxing in that it eliminates those latent waxes in the citrus oil which are not precipitated during the chilling process. The process of the invention may be carried out either before or after a conventional chilling-dewaxing process to yield a citrus oil which will remain substantially sediment-free for extended periods during storage.

Where the process of the invention is carried out on a finished oil (i-e-, one which has already been dewaxed by a conventional chilling process), preferably the process includes a washing step to remove remaining diols after the oil is treated with the acidic solution and isolated. The isolated citrus oil is washed of excess diols by mixing it with an aqueous washing solution, which can be either pure water or an acidic solution. The citrus oil and aqueous washing solution are then separated. This is followed by centrifugation to separate and remove precipitates to yield clear citrus oil.

Where the process of the invention is carried out on an unfinished oil emulsion (i.e., one which has not yet been dewaxed by a conventional chilling process), there is no need to conduct a washing step since most of the residual diols (unlike their epoxide precursors) can now be effectively removed by conventional chilling-dewaxing.

DETAILED DESCRIPTION OF THE INVENTION

In accordance with the invention, a conventional chilling-dewaxing process for citrus oils is supplemented by subjecting a citrus oil to either a pre-chilling-dewaxing or post-chilling-dewaxing treatment step designed to eliminate, e.g. by precipitation, latent sediment-forming components of the oil which generally do not precipitate out of the oil merely upon chilling. Psoralen epoxides, which occur naturally in citrus oils, are examples of latent sediment-forming materials because they do not precipitate out of the oil upon chilling, yet during storage they gradually undergo hydrolysis to the corresponding diols, which are much less soluble in the oil.

In the treatment step of the invention, relatively hydrophobic psoralen epoxides in the citrus oil are converted to relatively hydrophilic diols by mixing the citrus oil with an acidic aqueous treatment solution. The treatment is conducted under conditions and for a duration which is sufficient to convert substantially all of the psoralen epoxides to diols. The relatively hydrophobic epoxides are more soluble in the citrus oil phase than in the aqueous phase. On the other hand, the relatively hydrophilic reaction products (i.e., diols) are more soluble in the aqueous phase and less soluble in the citrus oil than are their epoxide precursors. Consequently, the conversion of the relatively hydrophobic epoxides to the relatively hydrophilic diols is accompanied by expulsion of the diols from the oil, either through direct precipitation or preferential dissolution into the aqueous phase (or both). In this manner, the relatively hydrophobic psoralen epoxides are removed from the citrus oil phase upon their conversion to the relatively hydrophilic diols.

Thus, upon treating a citrus oil with an acidic aqueous treatment solution in accordance with the invention, the psoralen epoxides undergo an accelerated hydrolysis reaction wherein the epoxide groups are rapidly converted to diols. The resulting diol compounds are relatively hydrophilic and are thus precipitated and/or preferentially dissolved in the acidic aqueous treatment solution (which is easily separated from the citrus oil and removed, thereby removing the latent sediment-forming materials from the oil).

Citrus oils which may be treated in accordance with the invention include lemon oil, lime oil, tangerine oil, orange oil, grapefruit oil and bergamot oil.

The method of the invention may be applied to incompletely processed citrus oils (i.e., emulsified mixtures of oil, water, and peel solids which have not been subjected to the final stage of centrifugation required to yield pure oil, and which therefore have also not undergone conventional chilling-dewaxing). Alternatively, the process of the invention may be conducted on finished oils stored in inventory which have already undergone a conventional chilling-dewaxing process.

The specific acid used in the acidic aqueous treatment solution of the invention should be selected based upon the compatibility of the acid with the final product. For example, if the citrus oil is to be used in food products, the acid should be a food grade material. If the citrus oil is to be used in fragrances and other products to be applied to the skin, the acid should not be a skin irritant. Acids which may be used in the practice of the invention include hydrochloric acid, phosphoric acid and citric acid, which are all food grade materials.

Citric acid is the preferred acid for use in the invention because it has been extensively evaluated and shown not to adversely affect the flavor of the oil. In addition, citric acid solubilizes the resulting diols in the aqueous phase, facilitating their extraction. The mineral acids, hydrochloric and phosphoric acid, do not have this solubilizing effect; nevertheless, they are suitable. However, sulfuric acid should be avoided since its use may result in unwanted reactions with components of the citrus oil.

The effectiveness of the treatment step is also dependent upon the pH of the acidic aqueous treatment solution, the duration of the treatment, and the volume ratio of treatment solution to citrus oil. As will be appreciated by those skilled in the art who practice this invention, these three factors are interdependent. For example, the higher the pH of the acidic treating solution, the longer the treatment duration and the greater the ratio of treatment solution to citrus oil which will be required to effect conversion of the psoralen epoxides to diols. It is desirable to minimize the treatment time because prolonged exposure of the citrus oil to the acidic solution may result in unwanted side reactions and off flavors. In addition, it is desirable to minimize the volume ratio of treatment solution to citrus oil for the sake of economy of resources and ease of separation of the aqueous phase from the oil. For these reasons, very low pHs for the treatment solution on the order of less than 1.0 are most preferred.

To illustrate the relationship between these factors, take the case of a finished lemon oil treated with a solution of 50% citric acid and 50% water, the solution having a pH of about 0.5. A treatment for about 2 hours using 1 part by volume of this solution per 20 parts by volume lemon oil has proven to be effective in converting substantially all of the psoralen epoxides to diols.

However, in the case of only a 6% citric acid treatment solution, having a pH of about 2.0, a much longer treatment time of about 24 hours and a much higher solution-to-oil volume ratio of 1:1 is required to achieve the same result. Therefore, use of the lower pH solution is very much preferred.

As a practical matter, the present invention requires a solution having a pH of less than about 2.5 in order to effect a substantially complete conversion of psoralen epoxides to diols within a reasonable period of time. The preferred pH for the acidic aqueous treatment solution is less than 1.5, more preferably less than 1.0, and most preferably about 0.5 (corresponding, for example, to a citric acid concentration in the water of about 50% by weight).

If the citrus oil to be treated is in the form of a finished oil, the acidic aqueous treatment solution of desired pH is directly mixed with the oil. If the citrus oil to be treated is a freshly produced emulsion, the acid is added to the emulsion in pure form and in an amount necessary to provide the desired pH, based on the water content of the emulsion. In order to achieve the most preferred pH of about 0.5, citric acid is added in an amount to create a 50 wt. % concentration in the water.

Thus, according to the invention, a citrus oil is mixed with an aqueous acid solution having a pH and in an amount which is sufficient to convert substantially all of the psoralen epoxides in the citrus oil to diols, over a reasonably short period of time (e.g., less than 24 hours, preferably within 2–3 hours). In this manner, psoralen epoxides are removed from the citrus oils in a simple, cost-effective fashion.

The temperature of the treatment step is preferably any typical ambient room temperature (e.g., 50° F. to 80° F.). Heating to elevated temperatures should be avoided as this will have an adverse effect on the volatiles content of the oil.

The volume ratio of the acidic aqueous treatment solution relative to the citrus oil is preferably optimized for the particular application at hand. As discussed above, the ratio which will be necessary to effect conversion of substantially all of the psoralen epoxides in a reasonably short period of time depends upon the pH of the solution. Thus, optimum volume ratios will become apparent to those skilled in the art who practice the invention. In the case of a citric acid treatment solution having a pH of about 0.5, the preferred volume ratio of treatment solution to lemon oil is about 1:20. This has been found to effect complete conversion of the psoralen epoxides after about 2 hours of continuous mixing. As discussed above, higher ratios and longer times will be necessary if treatment solutions having a higher pH are utilized.

After treatment, the aqueous acidic treatment solution and the citrus oil are separated, preferably by allowing the mixture to settle for about one hour, then draining off the aqueous layer. However, if the two phases are emulsified or turbid, then a centrifugation step should be applied to yield a clear oil. The citrus oil recovered after separation is then preferably subjected to a conventional chilling-dewaxing process if such a process had not been conducted previously.

According to another embodiment of the invention, the process is supplemented with a washing step wherein the treated citrus oil is mixed with a washing solution so as to wash or extract excess diols which remain after treatment with the acidic solution. In the case of a finished citrus oil (i.e., one which has already been subjected to conventional chilling-dewaxing), the process is conducted as follows. First, an aqueous acidic treatment solution is mixed with the finished oil under conditions described above so as to convert the psoralen epoxides in the finished oil to diols, which are precipitated directly and/or are extracted from the citrus oil by the aqueous phase. The mixture is then allowed to settle and the aqueous phase is drained off. The treated citrus oil is then washed to remove excess diols by mixing the oil with water, or preferably an aqueous acidic washing solution. After settling, the aqueous phase is drained off and the remaining oil phase is centrifuged to yield a clear oil.

The washing solution can be water (either tap water or distilled water), but it is preferably an acidic aqueous solution having the same composition and pH as the treatment solution. Use of an acidic washing solution is preferred because, in addition to washing diols, it will also convert any remaining psoralen epoxides which may have escaped conversion during the preceding treatment step, to diols. If an acidic aqueous washing solution is selected, the preferred pH for the washing solution is less than about 2.5 and most preferably about 0.5 (corresponding, for example, to a citric acid concentration in water of 50% by weight). The acidic aqueous washing solution of desired pH is directly mixed with the treated and isolated citrus oil.

As in the case of the treatment step, the duration of the washing step, the volume ratio of washing solution to citrus oil, and the pH of the washing solution are interdependent and they can be optimized for the particular application at hand. In addition, the optimum washing duration and optimum volume ratio of washing solution to oil will depend on the composition of the washing solution. For example, where an aqueous citric acid solution having a pH of about 0.5 is employed as the washing solution, an effective washing can be done using the washing solution in a volume ratio of only 1:20 relative to the volume of citrus oil, and washing can be completed in about one hour. Only a small volume ratio is necessary because 50% by weight aqueous citric acid is an excellent solvent for the diols. However, if pure water is used as the washing solution, the volume ratio of washing solution to citrus oil should be much greater, preferably about 1:1, to effectively wash the diols, because pure water does not solubilize the diols to the same extent as a solution of citric acid. Thus, citric acid allows for the use of much smaller volumes of washing solution, and it is preferred for this reason.

After the citrus oil has been subjected to the wash step, the two phases are separated. The phases are preferably separated by letting the mixture settle overnight, followed by draining, followed by centrifugation to yield a clear oil. Unlike in the case of a finished citrus oil, in the case of an incompletely processed citrus oil emulsion, a washing step has proven to be superfluous and unnecessary. This is because excess diols remaining in the oil after acid solution treatment will be effectively removed during the conventional chilling-dewaxing step which will now follow to finish the oil. Typical conditions for chilling-dewaxing are well known to those skilled in the art and need not be described herein.

When a susceptible citrus oil is treated in accordance with the present invention, an oil of greatly reduced sedimentation potential and reduced phototoxicity is produced. Psoralen epoxides in the oils are converted to diols in a quick and controlled manner. The epoxide-to-diol transformation is effected by contacting citrus oils with an acidic aqueous treatment solution. Depending upon the specific treatment solution used, the diols are either expelled as a solid precipitate or solubilized by the treatment solution, or both. By this process, epoxides are inexpensively eliminated from the citrus oils. At the same time, the treatment does not result in any deleterious change in the volatiles content of the citrus oil and the treatment has no effect on the taste and aroma of the oil.

EXAMPLES

The following examples illustrate preferred solutions and conditions for treating and washing a finished lemon oil and for treating an incompletely processed lemon oil emulsion. These examples should be regarded in an illustrative rather than a restrictive sense.

Treatment of a Finished Oil

A finished lemon oil which had been previously dewaxed by chilling was combined with an aqueous citric acid treatment solution in a volume ratio of 20 parts by volume oil to 1 part by volume treatment solution. The treatment solution was 50 weight % citric acid and 50 weight % water which resulted in a pH of about 0.5. The lemon oil-citric acid solution mixture was agitated continuously for two hours at room temperature. Agitation was then suspended. After the mixture was allowed to settle for about 1 hour, the aqueous citric acid treatment solution, which was the bottom phase, was drained off.

The treated lemon oil was then combined with an aqueous citric acid washing solution in a volume ratio of 20 parts by volume oil to 1 part by volume washing solution. The washing solution was 50 weight % citric acid and 50 weight % water, imparting a pH of about 0.5 to the solution. The lemon oil-washing solution mixture was agitated for one hour at room temperature. Agitation was then suspended. After the mixture was allowed to settle overnight, the aqueous citric acid washing solution was drained off. The washed citrus oil was then centrifuged to yield a clear, purified lemon oil which was substantially free of psoralen epoxides and diols. The finished lemon oil remained sediment-free during subsequent storage.

Treatment of an Incompletely Processed Oil Emulsion

The relative water and oil contents of an incompletely processed lemon oil emulsion were determined and sufficient solid citric acid was added to the emulsion to produce an aqueous phase of 50 weight % citric acid and 50 weight % water. The oil was then agitated continuously for two hours at room temperature, followed by centrifugation to yield a clear lemon oil. The clarified oil was then subjected to a conventional chilling-dewaxing process in which the oil was treated in a known manner (i.e., chilling and centrifuging) to precipitate and remove waxes. No washing step was required. The finished lemon oil remained sediment-free during storage for extended periods.

What is claimed is:

1. A process for treating a citrus oil comprising the steps of:
   mixing a volume of a citrus oil containing psoralen epoxides with a volume of an acidic aqueous treatment solution, comprising water and an acid, for a period of time which is sufficient to convert substantially all of said epoxides to diols; and
   separating the citrus oil from the acidic aqueous treatment solution.

2. The process of claim 1 wherein the acid is selected from the group consisting of citric acid, hydrochloric acid and phosphoric acid.

3. The process of claim 1 wherein the acid is citric acid.

4. The process of claim 1 wherein the acidic aqueous treatment solution has a pH of less than about 2.5.

5. The process of claim 3 wherein the acidic aqueous treatment solution has a pH of less than about 2.5.

6. The process of claim 1 wherein the acidic aqueous treatment solution has a pH of less than 1.0.

7. The process of claim 3 wherein the acidic aqueous treatment solution has a pH of less than 1.0.

8. The process of claim 1 wherein the acidic aqueous treatment solution has a pH of about 0.5.

9. The process of claim 3 wherein the acidic aqueous treatment solution has a pH of about 0.5.

10. The process according to claim 5 wherein said volume of citrus oil and said volume of treatment solution have a volume ratio of about 1:1.

11. The process according to claim 10 wherein the step of mixing is conducted for a period of less than 36 hours.

12. The process according to claim 9 wherein said volume of citrus oil and said volume of treatment solution have a volume ratio of greater than about 10:1.

13. The process according to claim 12 wherein said volume of citrus oil and said volume of treatment solution have a volume ratio of about 20:1.

14. The process according to claim 12 wherein the step of mixing is conducted for a period of less than 3 hours.

15. The process according to claim 1 further comprising the steps of washing the citrus oil which has been separated from the treatment solution with a washing solution so as to dissolve diols into the washing solution, and separating the citrus oil from the washing solution containing diols.

16. The process of claim 15 wherein the washing solution is water.

17. The process of claim 15 wherein the washing solution comprises citric acid and water.

18. The process of claim 1 wherein the treatment solution comprises from about 5% to about 50% by weight of citric acid in water.

19. The process of claim 18 wherein the citrus oil is lemon oil.

20. A process for extracting psoralen epoxides from a citrus oil comprising the steps of: mixing a citrus oil containing psoralen epoxides with an acidic aqueous treatment solution comprising water and an acid, the treatment solution having a pH of no greater than about 2.0, to convert psoralen epoxides to corresponding diols, followed by separating the citrus oil from the treatment solution.

21. The process of claim 20 wherein the step of mixing is conducted for a period of time which is sufficient to convert substantially all of the psoralen epoxides to diols.

22. The process of claim 20 wherein the acid is selected from the group consisting of citric acid, hydrochloric acid and phosphoric acid.

23. The process of claim 20 wherein the acid is citric acid.

24. The process of claim 22 wherein the acidic aqueous treatment solution has a pH of less than 1.0.

25. The process of claim 22 wherein the acidic aqueous treatment solution has a pH of about 0.5.

26. The process of claim 20 wherein the step of mixing is conducted for a period of less than 36 hours.

27. The process of claim 25 wherein the step of mixing is conducted for a period of less than 3 hours.

28. The process of claim 20 wherein the step of mixing is conducted with from about 1:20 parts by volume of treatment solution to citrus oil to about 1:1 parts by volume of treatment solution to citrus oil.

29. The process of claim 20 further comprising the steps of washing the citrus oil which has been separated from the treatment solution with a washing solution so as to dissolve diols into the washing solution, and separating the citrus oil from the washing solution containing diols.

30. The process of claim 29 wherein the washing solution comprises citric acid and water.

31. A citrus oil treated by the process of claim 20.

32. A process for dewaxing an emulsion of water and a citrus oil containing psoralen epoxides comprising the steps of: adding an acid to the emulsion in an amount which is sufficient to impart a pH of less than about 2.0 to an aqueous phase of the emulsion; mixing the acid and emulsion together to convert psoralen epoxides to diols; separating the citrus oil from the aqueous phase; chilling the separated citrus oil to precipitate waxes; and removing the precipitated waxes from the citrus oil.

33. The process of claim 32 wherein the step of mixing is conducted for a period of time which is sufficient to convert substantially all of said psoralen epoxides to diols.

34. The process of claim 33 wherein the acid is citric acid.

35. The process of claim 34 wherein the acid is added to attain a pH of less than 1.0 in the aqueous phase.

36. The process of claim 35 wherein the acid is added to attain a pH of about 0.5 in the aqueous phase.

* * * * *

UNITED STATES PATENT AND TRADEMARK OFFICE
CERTIFICATE OF CORRECTION

PATENT NO.   :   5,362,714
DATED        :   November 8, 1994
INVENTOR(S)  :   RADFORD, et al.

It is certified that error appears in the above-indentified patent and that said Letters Patent is hereby corrected as shown below:

Column 10, line 14 "33" should be --32--.

Signed and Sealed this

Eleventh Day of April, 1995

Attest:

BRUCE LEHMAN

*Attesting Officer*     *Commissioner of Patents and Trademarks*